United States Patent [19]

Saville

[11] Plant 5,044

[45] May 3, 1983

[54] ROSE PLANT

[75] Inventor: F. Harmon Saville, Rowley, Mass.

[73] Assignee: Nor'East Miniature Roses, Inc., Rowley, Mass.

[21] Appl. No.: 307,380

[22] Filed: Oct. 1, 1981

[51] Int. Cl.[3] ..... A01H 5/00

[52] U.S. Cl. ..... Plt./7

[58] Field of Search ..... Plt./7

*Primary Examiner*—Robert E. Bagwill

*Attorney, Agent, or Firm*—Vincent G. Gioia

[57] ABSTRACT

A new miniature rose variety of bright Indian orange coloring borne singly and in large sprays.

1 Drawing Figure

The present invention relates to a new and distinct variety of rose plant of the miniature rose class, which was originated by my crossing as seed parent the rose known as "Sheri Anne" (U.S. Plant Pat. No. 3,826) and the deep yellow floribunda "Glenfiddich" as pollen parent.

Among the novel characteristics possessed by this new variety which distinguish it from its parents and all other varieties of which I am aware are flowers of bright Indian orange coloring unusual in a miniature rose. Flowers are borne singly and in large sprays. The flower's unique coloring is attractively contrasted against dark glossy green foliage. Asexual reproduction by budding of the new variety as performed in Essex County, Mass., shows that the foregoing and other distinguishing characteristics come true to form and are established and transmitted through succeeding propagations.

The accompanying drawing shows typical specimens of the vegetative growth and flowers of the new variety in different stages of development and as depicted in color as nearly true as it is reasonably possible to make the same in a color illustration of this character.

The following is a detailed description of my new variety, with color terminology in accordance with The Royal Horticultural Society Colour Chart (RHSCC). The terminology used in color description herein refers to plate numbers in the aforementioned color chart, e.g., "32A" is plate 32A of the Royal Horticultural Society Colour Chart.

Parentage: Seedling.
*Seed parent.*—"Sheri Anne".
*Pollen parent.*—"Glenfiddich".
Class: Miniature.

The following observations are made of specimens grown outdoors in Essex County, Mass. during the month of July.

FLOWER

Blooming habit: Continuous.

A. Bud:
(1) *Size.*—Medium.
(2) *Form.*—Short pointed, ovate.
(3) *Color.*—When sepals first divide — 32A.
(4) *Sepals.*—Slightly longer than bud, foliated.
(5) *Peduncle.*—Length — $\frac{3}{4}$ to 1 inch. Aspect — straight. Strength — erect. Color — 144B.

B. Bloom:

(1) *Size.*—Average size when fully expanded — about 1 to $1\frac{1}{4}$ inches.
(2) *Borne.*—Singly and in sprays of 3 to 15 blooms.
(3) *Form.*—Low centered at first opening to a flat ruffled bloom with numerous petalloids.
(4) *Petalage.*—Number of petals under normal conditions — about 45 to 50.
(5) *Color.*—Indian orange bud 32A opens to Indian orange blooms with numerous petalloids in open bloom. Overall bright orange coloring is very apparent with deeper tones when petals are bunches as in $\frac{1}{4}$ open flower stage. Overall tonality of $\frac{3}{4}$ to fully open bloom is 32B to 32D which lighten upon aging. Base of petal at point of attachment is light yellow. Individual petals show veining.

C. Petals:
(1) *Texture.*—Firm.
(2) *Appearance.*—Satiny.
(3) *Form.*—Wide oval nearly round quilling to points.
(4) *Arrangement.*—Regularly arranged, shingle-like.
(5) *Petaloids in center.*—Many.
(6) *Persistence.*—Drop off cleanly.
(7) *Fragrance.*—Medium sweet.
(8) *Lasting quality.*—Long lasting on plant.

REPRODUCTIVE ORGANS

A. Stamens, filaments and anthers:
(1) *Arrangement.*—Stamens regular, scattered around styles and petalloids.
(2) *Color.*—17B.

B. Pollen:
*Color.*—17A.

C. Styles: Bunched, even length.

D. Stigmas:
*Color.*—11A.

E. Hips:
*Shape.*—Globular.
*Size.*—Small to medium.
*Color.*—Orange.
*Do seeds protrude?*—Not usually.

PLANT

A. Form: Compact, very bushy.

B. Growth: Vigorous, uniform branching.
*Height attained.*—About 12 to 14 inches.

C. Foliage: Compound 5 to 7 leaflets.
(1) *Size.*—Medium.

(2) *Quantity.*—Abundant, profuse.
(3) *Color.*—Foliage: Dark green.
(4) *Shape.*—Long, oval, pointed, acuminate.
(5) *Texture.*—Upper side is glossy and under side is satiny.
(6) *Edge.*—Serrate.
(7) *Serration.*—Large.
(8) *Leaf stem.*—Color — green with wine red cast.
(9) *Stipules.*—Medium, smooth.
(10) *Resistance to disease.*—Blackspot — average. Mildew — average. Rust — average.

D. Wood:
(1) *New wood.*—Color — near 146C. Bark — smooth.
(2) *Old wood.*—Color — near 141A. Bark — smooth.

E. Thorns:
(1) *Thorns.*—Quantity (main stalk): very few. On laterals from stalk — average. Form — long thin pointed, angled slightly downward. Length — medium. Color — near 187B. Position — irregular.
(2) *Prickles.*—None.

F. Winter hardiness: Average.

I claim:

1. A new and distinct variety of rose plant of the miniature class, substantially as shown and described, characterized particularly by unusual, bright Indian orange blooms borne singly and in large sprays (3 to 15 blooms).

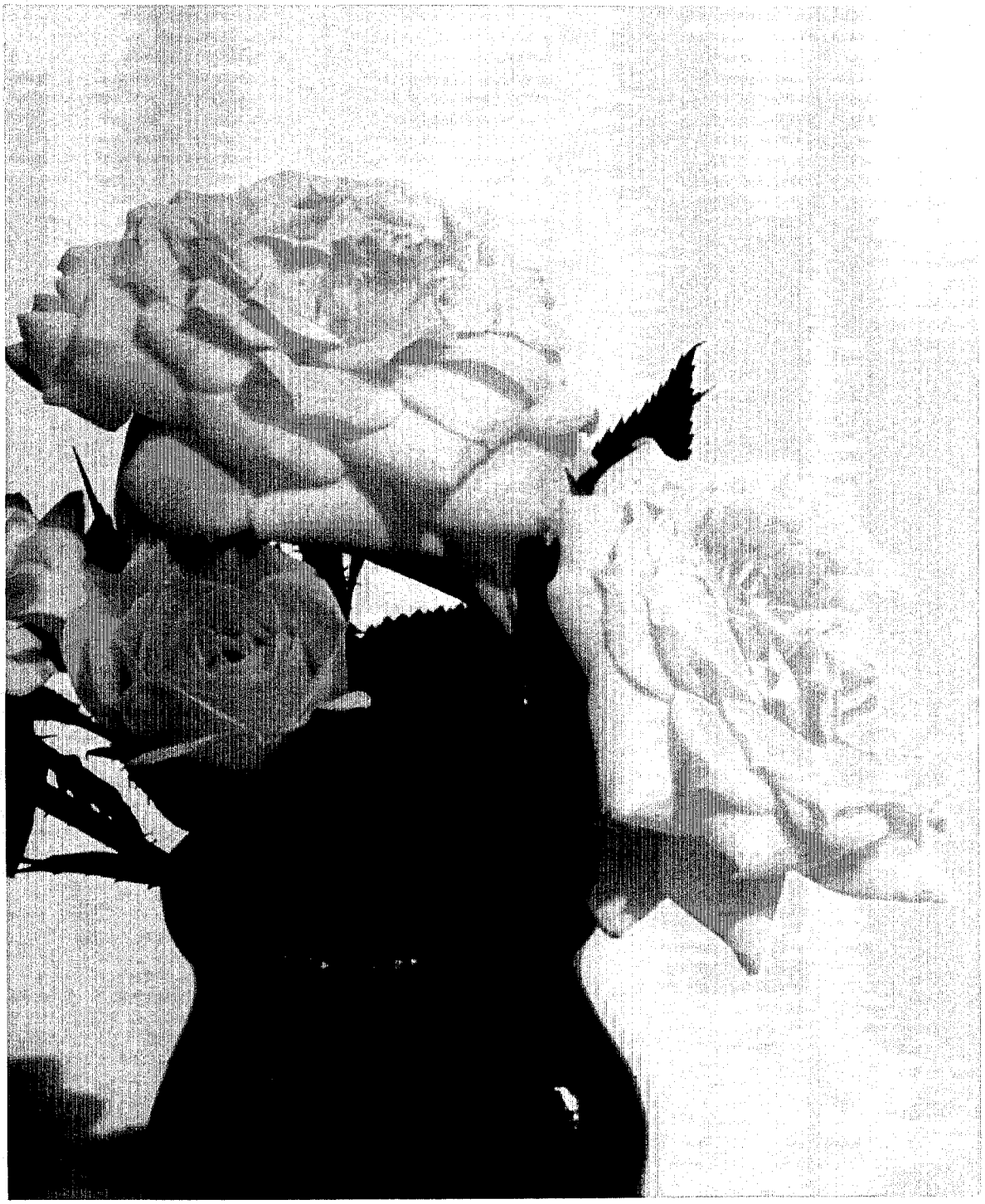

* * * * *